(12) United States Patent
Ingimundarson et al.

(10) Patent No.: US 9,220,625 B2
(45) Date of Patent: Dec. 29, 2015

(54) THORACIC LUMBAR SACRAL ORTHOSIS

(71) Applicant: OSSUR hf, Reykjavik (IS)

(72) Inventors: Arni Thor Ingimundarson, Gardabaer (IS); Brice Robertson, Sunnyvale, CA (US); Harry Duane Romo, Aliso Viejo, CA (US)

(73) Assignee: OSSUR HF, Reykjavik (IS)

( * ) Notice: Subject to any disclaimer, the term of this patent is extended or adjusted under 35 U.S.C. 154(b) by 0 days.

(21) Appl. No.: 14/173,329

(22) Filed: Feb. 5, 2014

(65) Prior Publication Data

US 2014/0155798 A1    Jun. 5, 2014

Related U.S. Application Data

(63) Continuation of application No. 12/938,593, filed on Nov. 3, 2010, now Pat. No. 8,657,769.

(60) Provisional application No. 61/323,414, filed on Apr. 13, 2010, provisional application No. 61/258,078, filed on Nov. 4, 2009.

(51) Int. Cl.
*A61F 5/02* (2006.01)
*A61F 5/30* (2006.01)

(52) U.S. Cl.
CPC . *A61F 5/02* (2013.01); *A61F 5/024* (2013.01); *A61F 5/30* (2013.01)

(58) Field of Classification Search
USPC .................. 602/5–6, 14, 16–22, 27–28; 2/45; 128/95.1, 96.1, 98.1, 99.1, 100.1, 128/101.1, 102.1, 103.1
See application file for complete search history.

(56) References Cited

U.S. PATENT DOCUMENTS

| | | | |
|---|---|---|---|
| 7,916 | A | 1/1851 | Knapp |
| 61,487 | A | 1/1867 | Vollschwitz |
| 181,948 | A | 9/1876 | Kleinschuster |
| 232,420 | A | 9/1880 | Smith |
| 321,145 | A | 6/1885 | Spencer |
| 321,146 | A | 6/1885 | Spencer |

(Continued)

FOREIGN PATENT DOCUMENTS

| | | |
|---|---|---|
| AU | 2010271020 A1 | 2/2012 |
| AU | 2010271020 A2 | 2/2012 |

(Continued)

OTHER PUBLICATIONS

Pamplet—"Bledsoe Phillippon K.A.F. Positioning Kit, Application Instructions (CP020205 Rev Apr. 2007), New Hip Arthroscopy Padding and Positioning Kit", Council Directive 93/42/EEC of Jun. 14, 1993 concerning Medical Devices, 2 pages.

(Continued)

*Primary Examiner* — Ophelia A Hawthorne
(74) *Attorney, Agent, or Firm* — Workman Nydegger

(57) ABSTRACT

A thoracic lumbar sacral orthosis includes an upper body support for use with a torso orthosis. The upper body support has an anterior assembly including an anterior plate secured to the torso orthosis, a sternal assembly connected to the anterior plate, and a pectoral assembly connected to the sternal assembly. A posterior assembly is connected to the torso orthosis and is connected to the pectoral assembly by at least one strap. The sternal assembly has at least one pivot point arranged to pivot the sternal assembly relative to the anterior plate.

20 Claims, 12 Drawing Sheets

(56) References Cited

U.S. PATENT DOCUMENTS

| | | | |
|---|---|---|---|
| 328,638 A | 10/1885 | Battershall | |
| 368,699 A | 8/1887 | Zervas | |
| 386,642 A | 7/1888 | Mann | |
| 507,172 A | 10/1893 | Shelden | |
| 571,749 A | 11/1896 | Colton | |
| 596,849 A | 1/1898 | Combier | |
| 601,446 A | 3/1898 | Mestler | |
| 616,196 A | 12/1898 | Medbury | |
| 629,900 A | 8/1899 | Fosburgh | |
| 639,072 A | 12/1899 | Lyons | |
| 664,250 A | 12/1900 | Fitzpatrick | |
| 709,055 A | 9/1902 | Sheldon | |
| 714,124 A | 11/1902 | Adams | |
| 746,563 A | 12/1903 | McMahon | |
| 772,926 A | 10/1904 | Colton | |
| 787,894 A | 4/1905 | Colton | |
| 888,490 A | 5/1908 | Haas | |
| 894,066 A | 7/1908 | Scapra | |
| 1,124,596 A | 1/1915 | Dalpe | |
| 1,316,915 A | 9/1919 | Meyer et al. | |
| 1,393,188 A | 10/1921 | Whiteman | |
| 1,463,579 A | 7/1923 | Funck | |
| 1,469,661 A | 10/1923 | Migita | |
| 1,481,903 A | 1/1924 | Hart | |
| 1,530,713 A | 3/1925 | Clark | |
| 1,558,661 A | 10/1925 | Yeganian | |
| 1,755,641 A | 4/1930 | Foulke | |
| 1,948,785 A | 2/1934 | Dondelinger | |
| 1,981,157 A | 11/1934 | Walter | |
| 2,036,484 A | 4/1936 | Le May | |
| 2,100,964 A | 11/1937 | Kendrick | |
| 2,117,309 A | 5/1938 | Fritsch | |
| 2,219,475 A | 10/1940 | Flaherty | |
| 2,409,381 A | 10/1946 | Pease, Jr. | |
| 2,543,370 A | 2/1951 | Kludt et al. | |
| 2,554,337 A | 5/1951 | Lampert | |
| 2,630,801 A | 3/1953 | Mest et al. | |
| 2,749,550 A | 6/1956 | Pease | |
| 2,793,368 A | 5/1957 | Nouel | |
| 2,808,050 A | 10/1957 | Ward | |
| 2,815,021 A | 12/1957 | Freeman | |
| 2,828,737 A | 4/1958 | Hale | |
| 2,904,040 A | 9/1959 | Hale | |
| 2,906,260 A | 9/1959 | Myers | |
| 2,906,261 A | 9/1959 | Craig | |
| 3,095,875 A | 7/1963 | Davidson et al. | |
| 3,096,760 A | 7/1963 | Nelkin | |
| 3,128,514 A | 4/1964 | Parker et al. | |
| 3,274,996 A | 9/1966 | Jewett | |
| 3,282,264 A | 11/1966 | Connelly | |
| 3,351,053 A | 11/1967 | Stuttle | |
| 3,371,351 A | 3/1968 | Allain | |
| 3,434,469 A | 3/1969 | Swift | |
| 3,480,012 A | 11/1969 | Smithers et al. | |
| 3,509,875 A | 5/1970 | Richter | |
| 3,548,817 A | 12/1970 | Mittasch | |
| 3,563,431 A | 2/1971 | Pletz | |
| 3,570,480 A | 3/1971 | Stubbs | |
| 3,578,773 A | 5/1971 | Schultz | |
| 3,762,421 A | 10/1973 | Sax, Sr. | |
| 3,771,513 A | 11/1973 | Velazquez | |
| 3,812,850 A | 5/1974 | Reiman | |
| 3,834,048 A | 9/1974 | Maurer | |
| 3,902,503 A | 9/1975 | Gaylord, Jr. | |
| 3,920,008 A | 11/1975 | Lehman | |
| 3,927,665 A | 12/1975 | Wax | |
| 3,945,376 A * | 3/1976 | Kuehnegger | 602/19 |
| 4,055,168 A | 10/1977 | Miller et al. | |
| 4,099,524 A | 7/1978 | Cueman et al. | |
| 4,114,788 A | 9/1978 | Zufich | |
| 4,173,973 A | 11/1979 | Hendricks | |
| 4,175,553 A | 11/1979 | Rosenberg | |
| 4,230,101 A | 10/1980 | Gold | |
| 4,285,336 A | 8/1981 | Oebser et al. | |
| 4,383,523 A | 5/1983 | Schurman | |
| 4,392,489 A | 7/1983 | Wagner, Sr. | |
| RE31,564 E | 4/1984 | Hendricks | |
| 4,475,543 A | 10/1984 | Brooks et al. | |
| 4,494,536 A | 1/1985 | Latenser | |
| 4,502,471 A | 3/1985 | Owens | |
| 4,508,110 A | 4/1985 | Modglin | |
| 4,559,933 A * | 12/1985 | Batard et al. | 602/19 |
| 4,569,336 A | 2/1986 | Wheeler | |
| 4,574,789 A | 3/1986 | Forster | |
| 4,608,971 A | 9/1986 | Borschneck | |
| 4,628,913 A | 12/1986 | Lerman | |
| 4,640,269 A | 2/1987 | Goins | |
| 4,648,390 A | 3/1987 | Friddle | |
| 4,649,574 A | 3/1987 | Michels | |
| 4,658,807 A | 4/1987 | Swain | |
| 4,677,699 A | 7/1987 | Barabe | |
| 4,677,969 A | 7/1987 | Calabrese | |
| 4,691,696 A | 9/1987 | Farfan de los Godos | |
| 4,696,291 A | 9/1987 | Tyo | |
| 4,697,592 A | 10/1987 | Maddux et al. | |
| 4,796,610 A | 1/1989 | Cromartie | |
| 4,805,605 A | 2/1989 | Glassman | |
| 4,807,605 A | 2/1989 | Mattingly | |
| 4,843,688 A | 7/1989 | Ikeda | |
| 4,862,878 A | 9/1989 | Davison et al. | |
| 4,870,761 A | 10/1989 | Tracy | |
| 4,905,678 A | 3/1990 | Cumins et al. | |
| 4,937,952 A | 7/1990 | Olivieri | |
| 4,976,257 A | 12/1990 | Akin et al. | |
| 5,027,482 A | 7/1991 | Torppey | |
| 5,072,725 A | 12/1991 | Miller | |
| 5,074,288 A | 12/1991 | Miller | |
| 5,105,828 A | 4/1992 | Grant | |
| 5,111,807 A | 5/1992 | Spahn et al. | |
| 5,120,288 A | 6/1992 | Sinaki | |
| 5,121,741 A | 6/1992 | Bremer et al. | |
| 5,135,470 A | 8/1992 | Reeves | |
| 5,135,471 A | 8/1992 | Houswerth | |
| 5,170,505 A | 12/1992 | Rohrer | |
| 5,171,296 A | 12/1992 | Herman | |
| 5,176,131 A | 1/1993 | Votel et al. | |
| D334,063 S | 3/1993 | DeWall | |
| 5,199,940 A | 4/1993 | Morris et al. | |
| 5,203,765 A | 4/1993 | Friddle, Jr. | |
| 5,215,518 A | 6/1993 | Rosen | |
| 5,226,874 A | 7/1993 | Heinz et al. | |
| 5,230,698 A | 7/1993 | Garth | |
| 5,259,831 A | 11/1993 | LeBron | |
| 5,259,833 A | 11/1993 | Barnett | |
| 5,295,947 A | 3/1994 | Muncy | |
| 5,313,952 A | 5/1994 | Hoch | |
| 5,318,575 A | 6/1994 | Chesterfield et al. | |
| 5,334,135 A | 8/1994 | Grim et al. | |
| 5,342,289 A | 8/1994 | Munny | |
| 5,346,461 A | 9/1994 | Heinz et al. | |
| 5,363,863 A | 11/1994 | Lelli et al. | |
| 5,368,552 A | 11/1994 | Williamson et al. | |
| 5,383,893 A | 1/1995 | Daneshvar | |
| 5,399,151 A | 3/1995 | Smith | |
| 5,421,809 A | 6/1995 | Rise | |
| 5,423,852 A | 6/1995 | Daneshvar | |
| 5,429,587 A | 7/1995 | Gates | |
| 5,435,015 A | 7/1995 | Ellis-Brewer | |
| 5,437,614 A | 8/1995 | Grim | |
| 5,437,617 A | 8/1995 | Heinz et al. | |
| 5,449,338 A | 9/1995 | Trudell | |
| 5,450,858 A | 9/1995 | Zablotsky et al. | |
| 5,466,214 A | 11/1995 | Calderon-Garciduenas | |
| 5,484,395 A | 1/1996 | DeRoche | |
| 5,499,965 A | 3/1996 | Sanchez | |
| 5,500,959 A | 3/1996 | Yewer, Jr. | |
| 5,503,314 A | 4/1996 | Fiscus | |
| 5,503,620 A | 4/1996 | Danzger | |
| 5,520,619 A | 5/1996 | Martin | |
| 5,522,792 A | 6/1996 | Bassett et al. | |
| 5,531,669 A | 7/1996 | Varnau | |
| 5,548,843 A | 8/1996 | Chase et al. | |
| 5,551,950 A | 9/1996 | Oppen | |
| 5,558,628 A | 9/1996 | Bzoch | |

(56) References Cited

U.S. PATENT DOCUMENTS

| | | | |
|---|---|---|---|
| 5,569,171 A | 10/1996 | Muncy | |
| 5,599,287 A | 2/1997 | Beczak, Sr. et al. | |
| 5,620,412 A | 4/1997 | Modglin | |
| 5,622,529 A | 4/1997 | Calabrese | |
| 5,632,724 A | 5/1997 | Lerman et al. | |
| 5,634,891 A | 6/1997 | Beczak, Sr. et al. | |
| 5,674,187 A | 10/1997 | Zepf | |
| 5,681,270 A | 10/1997 | Klearman et al. | |
| 5,685,831 A | 11/1997 | Floyd | |
| 5,688,137 A | 11/1997 | Bustance | |
| 5,690,260 A | 11/1997 | Aikins et al. | |
| 5,690,609 A | 11/1997 | Heize, III | |
| 5,695,452 A | 12/1997 | Grim et al. | |
| 5,704,904 A | 1/1998 | Dunfee | |
| 5,704,937 A | 1/1998 | Martin | |
| 5,708,977 A | 1/1998 | Morkunas | |
| 5,718,670 A | 2/1998 | Bremer | |
| 5,722,940 A | 3/1998 | Gaylord, Jr. et al. | |
| 5,724,993 A | 3/1998 | Dunfee | |
| 5,725,139 A | 3/1998 | Smith | |
| 5,728,054 A | 3/1998 | Martin | |
| 5,746,218 A | 5/1998 | Edge | |
| 5,752,640 A | 5/1998 | Prouix | |
| 5,778,565 A | 7/1998 | Holt et al. | |
| 5,782,782 A | 7/1998 | Miller | |
| 5,795,316 A | 8/1998 | Gaylord | |
| RE35,940 E | 10/1998 | Heinz et al. | |
| 5,816,251 A | 10/1998 | Glisan | |
| 5,823,981 A | 10/1998 | Grim et al. | |
| 5,826,766 A | 10/1998 | Aftanas | |
| 5,827,211 A | 10/1998 | Sellinger | |
| 5,830,167 A | 11/1998 | Jung | |
| 5,836,493 A | 11/1998 | Grunsted et al. | |
| 5,840,050 A | 11/1998 | Lerman | |
| 5,853,378 A | 12/1998 | Modglin | |
| 5,853,379 A | 12/1998 | Ostojic | |
| 5,857,988 A | 1/1999 | Shirley | |
| 5,868,292 A | 2/1999 | Stephens et al. | |
| 5,890,640 A | 4/1999 | Thompson | |
| 5,911,697 A | 6/1999 | Biedermann et al. | |
| 5,916,070 A | 6/1999 | Donohue | |
| 5,938,629 A | 8/1999 | Bloedau | |
| 5,950,628 A | 9/1999 | Dunfee | |
| 5,954,250 A | 9/1999 | Hall et al. | |
| 5,954,253 A | 9/1999 | Swetish | |
| 5,967,998 A | 10/1999 | Modglin | |
| 5,993,403 A | 11/1999 | Martin | |
| 6,010,472 A | 1/2000 | Schiller | |
| 6,027,466 A | 2/2000 | Diefenbacher et al. | |
| 6,029,273 A | 2/2000 | McCrane | |
| 6,036,664 A | 3/2000 | Martin, Sr. et al. | |
| 6,039,707 A | 3/2000 | Crawford et al. | |
| 6,063,047 A | 5/2000 | Minne | |
| 6,066,108 A | 5/2000 | Lundberg | |
| 6,070,776 A | 6/2000 | Furnary et al. | |
| 6,090,057 A | 7/2000 | Collins et al. | |
| 6,099,490 A | 8/2000 | Turtzo | |
| 6,110,138 A | 8/2000 | Shirley | |
| 6,117,096 A | 9/2000 | Hassard | |
| RE36,905 E | 10/2000 | Noble et al. | |
| 6,125,792 A | 10/2000 | Gee | |
| 6,129,691 A | 10/2000 | Rupert | |
| 6,156,001 A | 12/2000 | Frangi et al. | |
| 6,182,288 B1 | 2/2001 | Kibbee | |
| 6,190,343 B1 | 2/2001 | Heinz et al. | |
| D438,624 S | 3/2001 | Reina | |
| 6,213,968 B1 | 4/2001 | Heinz et al. | |
| 6,227,937 B1 | 5/2001 | Principe | |
| 6,245,033 B1 | 6/2001 | Martin | |
| 6,254,561 B1 | 7/2001 | Borden | |
| 6,289,558 B1 | 9/2001 | Hammerslag | |
| 6,315,746 B1 | 11/2001 | Garth et al. | |
| 6,322,529 B1 | 11/2001 | Chung | |
| 6,325,023 B1 | 12/2001 | Elnatan | |
| 6,338,723 B1 | 1/2002 | Carpenter et al. | |
| 6,419,652 B1 | 7/2002 | Slautterback | |
| 6,425,876 B1 | 7/2002 | Frangi et al. | |
| 6,428,493 B1 | 8/2002 | Pior et al. | |
| 6,432,073 B2 | 8/2002 | Pior et al. | |
| 6,471,665 B1 | 10/2002 | Milbourn et al. | |
| 6,478,759 B1 | 11/2002 | Modglin et al. | |
| 6,517,502 B2 | 2/2003 | Heyman et al. | |
| 6,540,703 B1 | 4/2003 | Lerman | |
| 6,589,195 B1 | 7/2003 | Schwenn et al. | |
| 6,602,214 B2 | 8/2003 | Heinz et al. | |
| 6,605,052 B1 | 8/2003 | Cool et al. | |
| 6,609,642 B2 | 8/2003 | Heinz et al. | |
| 6,623,419 B1 | 9/2003 | Smith et al. | |
| 6,652,596 B2 | 11/2003 | Smith et al. | |
| 6,676,617 B1 | 1/2004 | Miller | |
| 6,676,620 B2 | 1/2004 | Schwenn et al. | |
| 6,688,943 B2 | 2/2004 | Nagaoka | |
| 6,702,770 B2 | 3/2004 | Bremer et al. | |
| 6,726,643 B1 | 4/2004 | Martin | |
| 6,790,191 B1 * | 9/2004 | Hendricks | 602/19 |
| 6,802,442 B1 | 10/2004 | Thompson | |
| D499,806 S | 12/2004 | Machin et al. | |
| D501,078 S | 1/2005 | Cabana | |
| 6,893,098 B2 | 5/2005 | Kohani | |
| 6,913,585 B2 | 7/2005 | Salmon et al. | |
| 6,921,375 B2 | 7/2005 | Kihara | |
| 6,923,780 B2 | 8/2005 | Price et al. | |
| 6,926,685 B1 | 8/2005 | Modglin | |
| 6,936,021 B1 | 8/2005 | Smith | |
| 6,942,630 B2 | 9/2005 | Behan | |
| 6,951,547 B1 | 10/2005 | Park et al. | |
| 6,962,572 B1 | 11/2005 | Zahiri | |
| 6,964,644 B1 | 11/2005 | Garth | |
| 6,991,611 B2 | 1/2006 | Rhee | |
| 7,001,348 B2 | 2/2006 | Garth et al. | |
| 7,001,350 B2 | 2/2006 | Grosso | |
| 7,025,737 B2 | 4/2006 | Modglin | |
| 7,028,873 B1 | 4/2006 | Collier et al. | |
| 7,048,707 B2 | 5/2006 | Schwenn et al. | |
| 7,083,584 B2 | 8/2006 | Coligado | |
| 7,083,585 B2 | 8/2006 | Latham | |
| 7,087,032 B1 | 8/2006 | Ikeda | |
| 7,101,348 B2 | 9/2006 | Garth et al. | |
| 7,118,543 B2 | 10/2006 | Telles et al. | |
| 7,137,973 B2 | 11/2006 | Plauche et al. | |
| 7,140,691 B2 | 11/2006 | Kohani | |
| 7,166,083 B2 | 1/2007 | Bledsoe | |
| 7,186,229 B2 | 3/2007 | Schwenn et al. | |
| 7,201,727 B2 | 4/2007 | Schwenn et al. | |
| 7,306,571 B2 | 12/2007 | Schwenn et al. | |
| 7,309,304 B2 | 12/2007 | Stewart et al. | |
| 7,316,660 B1 | 1/2008 | Modglin | |
| 7,320,670 B1 | 1/2008 | Modglin | |
| 7,322,950 B2 | 1/2008 | Modglin | |
| 7,329,231 B2 | 2/2008 | Frank | |
| 7,473,235 B2 | 1/2009 | Schwenn et al. | |
| 7,476,185 B2 | 1/2009 | Drennan | |
| 7,549,970 B2 | 6/2009 | Tweardy | |
| 7,578,798 B2 | 8/2009 | Rhee | |
| 7,597,672 B2 | 10/2009 | Kruijsen et al. | |
| 7,600,660 B2 | 10/2009 | Kasper et al. | |
| 7,654,972 B2 | 2/2010 | Alleyne | |
| 7,662,121 B2 | 2/2010 | Zours | |
| 7,727,174 B2 | 6/2010 | Chang et al. | |
| 7,815,585 B2 | 10/2010 | Vollbrecht | |
| 7,819,831 B2 | 10/2010 | Dellanno | |
| 7,833,182 B2 | 11/2010 | Hughes | |
| 7,842,000 B2 | 11/2010 | Lai et al. | |
| 7,862,529 B2 | 1/2011 | Brown | |
| 7,871,388 B2 | 1/2011 | Brown | |
| 7,914,473 B2 | 3/2011 | Josey | |
| D636,494 S | 4/2011 | Garth et al. | |
| 8,006,877 B2 | 8/2011 | Lowry et al. | |
| 8,047,893 B2 | 11/2011 | Fenske | |
| 8,048,014 B2 | 11/2011 | Brown | |
| 8,066,161 B2 | 11/2011 | Green et al. | |
| 8,066,654 B2 | 11/2011 | Sandifer et al. | |
| 8,142,377 B2 | 3/2012 | Garth et al. | |
| 8,162,194 B2 | 4/2012 | Gleason | |

(56) References Cited

U.S. PATENT DOCUMENTS

| | | | |
|---|---|---|---|
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,303,528 B2 | 11/2012 | Ingimundarson et al. |
| 8,308,670 B2 | 11/2012 | Sandifer et al. |
| 8,308,869 B2 | 11/2012 | Gardner et al. |
| 8,372,023 B2 | 2/2013 | Garth et al. |
| 8,556,840 B2 | 10/2013 | Burke et al. |
| 8,597,222 B2 | 12/2013 | Lucero et al. |
| 8,795,215 B2 | 8/2014 | Rossi |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0148461 A1 | 10/2002 | Heinz et al. |
| 2002/0158097 A1 | 10/2002 | Beale |
| 2003/0000986 A1 | 1/2003 | Smith |
| 2003/0125650 A1 | 7/2003 | Grosso |
| 2003/0125705 A1 | 7/2003 | Ruman et al. |
| 2003/0220594 A1 | 11/2003 | Halvorson et al. |
| 2003/0229301 A1 | 12/2003 | Coligado |
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0228325 A1 | 10/2005 | Zours et al. |
| 2005/0240134 A1 | 10/2005 | Brown |
| 2005/0251074 A1 | 11/2005 | Latham |
| 2005/0267390 A1 | 12/2005 | Garth et al. |
| 2006/0011690 A1 | 1/2006 | Bareno |
| 2006/0052733 A1 | 3/2006 | Schwenn et al. |
| 2006/0064048 A1 | 3/2006 | Stano |
| 2006/0079821 A1 | 4/2006 | Rauch |
| 2006/0129077 A1 | 6/2006 | Parizot |
| 2006/0155229 A1 | 7/2006 | Ceriani et al. |
| 2006/0206992 A1 | 9/2006 | Godshaw et al. |
| 2007/0152007 A1 | 7/2007 | Kauss et al. |
| 2007/0179417 A1 | 8/2007 | Schwenn et al. |
| 2007/0185425 A1 | 8/2007 | Einarsson et al. |
| 2008/0195010 A1 | 8/2008 | Lai et al. |
| 2008/0208091 A1 | 8/2008 | Vollbrecht et al. |
| 2008/0249448 A1 | 10/2008 | Stevenson et al. |
| 2008/0262401 A1 | 10/2008 | Wagner et al. |
| 2008/0302839 A1 | 12/2008 | Murdoch et al. |
| 2009/0025115 A1 | 1/2009 | Duffy et al. |
| 2009/0030359 A1 | 1/2009 | Wikenheiser et al. |
| 2009/0062704 A1 | 3/2009 | Brown et al. |
| 2009/0082707 A1 | 3/2009 | Rumsey |
| 2009/0100649 A1 | 4/2009 | Bar et al. |
| 2009/0127308 A1 | 5/2009 | Mori et al. |
| 2009/0182253 A1 | 7/2009 | Grim et al. |
| 2009/0192425 A1 | 7/2009 | Garth et al. |
| 2009/0198166 A1 | 8/2009 | Shlomovitz |
| 2009/0275871 A1 | 11/2009 | Liu |
| 2009/0287128 A1 | 11/2009 | Ingimundarson et al. |
| 2010/0010568 A1 | 1/2010 | Brown |
| 2010/0037369 A1 | 2/2010 | Reichert |
| 2010/0204630 A1 | 8/2010 | Sandifer et al. |
| 2010/0217167 A1 | 8/2010 | Ingimundarson et al. |
| 2010/0256717 A1 | 10/2010 | Brown |
| 2010/0268141 A1 | 10/2010 | Bannister |
| 2010/0318010 A1 | 12/2010 | Sandifer et al. |
| 2011/0000005 A1 | 1/2011 | Brown |
| 2011/0009793 A1 | 1/2011 | Lucero et al. |
| 2011/0105971 A1 | 5/2011 | Ingimundarson et al. |
| 2011/0137221 A1 | 6/2011 | Brown |
| 2011/0144551 A1 | 6/2011 | Johnson |
| 2011/0152737 A1 | 6/2011 | Burke et al. |
| 2012/0022420 A1 | 1/2012 | Sandifer et al. |
| 2012/0197167 A1 | 8/2012 | Kruijsen et al. |
| 2012/0232450 A1 | 9/2012 | Garth et al. |
| 2012/0323154 A1 | 12/2012 | Ingimundarson et al. |
| 2013/0007946 A1 | 1/2013 | Brown |
| 2013/0012853 A1 | 1/2013 | Brown |
| 2013/0158457 A1 | 6/2013 | Garth et al. |
| 2013/0190670 A1 | 7/2013 | Von Zieglauer |
| 2013/0211302 A1 | 8/2013 | Brown |
| 2013/0237891 A1 | 9/2013 | Fryman et al. |
| 2013/0281901 A1 | 10/2013 | Ochoa |

FOREIGN PATENT DOCUMENTS

| | | |
|---|---|---|
| AU | 2010286851 A1 | 3/2012 |
| AU | 2010286851 A2 | 5/2012 |
| CA | 2767353 A1 | 1/2011 |
| CA | 2772296 A1 | 3/2011 |
| CN | 1311648 A | 9/2001 |
| CN | 201101603 Y | 8/2008 |
| CN | 102470040 A | 5/2012 |
| DE | 1 197 192 B | 7/1965 |
| DE | 8804683 U1 | 6/1988 |
| DE | 202 04 747 U1 | 7/2002 |
| DE | 10329454 A1 | 1/2005 |
| DE | 20 2004 015 328 U1 | 2/2005 |
| DE | 202005007124 U1 | 6/2005 |
| EP | 0657149 A1 | 6/1995 |
| EP | 1159940 A2 | 12/2001 |
| EP | 1588678 A1 | 10/2005 |
| EP | 1743608 A2 | 1/2007 |
| EP | 1985264 A1 | 10/2008 |
| EP | 2200545 A1 | 6/2010 |
| EP | 2451412 A1 | 5/2012 |
| EP | 2473072 A1 | 7/2012 |
| FR | 1 104 562 A | 11/1955 |
| FR | 2 757 073 A1 | 6/1998 |
| FR | 2 952 807 A1 | 5/2011 |
| GB | 909 970 A | 11/1962 |
| GB | 2133289 A | 7/1984 |
| JP | 2001204851 A | 7/2001 |
| JP | 2004209050 A | 7/2004 |
| JP | 2012011550 A | 1/2012 |
| JP | 2013503268 A | 1/2013 |
| JP | 2013536010 A | 9/2013 |
| WO | 2005086752 A2 | 9/2005 |
| WO | 2005086752 A3 | 9/2005 |
| WO | 2006121413 A1 | 11/2006 |
| WO | 2009017499 A1 | 2/2009 |
| WO | 2009017949 A1 | 2/2009 |
| WO | 2009052031 A1 | 4/2009 |
| WO | 2009068503 A1 | 6/2009 |
| WO | 2011005430 A1 | 1/2011 |
| WO | 2011025675 A1 | 3/2011 |
| WO | 2013016670 A1 | 1/2013 |

OTHER PUBLICATIONS

Charles T. Mehlman, John P. Schwegmann; Hyphenated History: Knight-Taylor Spinal Orthosis; American Journal of Orthopedics; Jun. 2000; pp. 479-483, vol. 29, Issue 6.

Pamphlet—"Bledsoe Phillippon K.A.F Positioning Kit", Bledsoe Brace Systems, Medical Technology Inc., 2004, 2 pages.

Posture Control Brace. Soft Form, Orthopaedic by Design, FLA Orthopedics, Inc., 1 page; 2004. http://www.flaorthopedics.com.

Michael Pfiefer, MD et al., "Effects of a New Spinal Orthosis on Posture, Trunk Strength, and Quality of Life in Women with Postmenopausal Osteoporosis—a Randomized Trial", American Journal of Physical Medicine & Rehabilitation, vol. 83, No. 3, Mar. 2004, USA, pp. 177-186.

Scoliosis Specialists. About the SpineCor Brace; 2006-2012; http://www.scoliosisspecialists.com/aboutspinecorbrace.html. Retrieved from Internet on Aug. 1, 2013.

(56) References Cited

OTHER PUBLICATIONS

International Search Report from PCT Application No. PCT/US2010/000601, Jun. 28, 2010.
International Preliminary Report on Patentability from PCT Application No. PCT/US2010/000601, Aug. 30, 2011.
Bledsoe Products, "Phillippon K.A.F. Positioning Kit". Http://bledsoebrace.com/products/kaf.asp [retrieved from the Internet May 10, 2012].
International Search Report and Written Opinion Issued in PCT/US2012/024619, May 16, 2012.
International Search Report and Written Opinion of the International Searching Authority Issued in PCT/US2012/043252, Jan. 10, 2013.
International Search Report from Corresponding PCT Application No. PCT/US2013/021170 dated Apr. 12, 2013.
Spinomed Brochure—Spinal Orthosis for Vertebral Extension in Osteoporosis; Stellar Orthotics and Prosthetics Group, 2 pages, retrieved from Internet Sep. 23, 2013. http://www.stellaroandp.com/spotlight.html.
Sato, Ena et al., "Effect of the WISH-type hip brace on functional mobility in patients with osteoarthritis of the hip: Evaluation using the time UP & GO", Prosthetics and Orthotics International 2012 36:25 originally published online Nov. 17, 2011, http://poi.sagepub.com/content/36/125 [retrieved from internet on Jan. 22, 2014].
Hsu et al., "Principles and components of spinal orthoses", AAOS Atlas of Orthoses and Assistive Devices, 4th Ed., Chapter 7, 2008, p. 89-111.
International Search Report from PCT Application No. PCT/US2010/002893, Feb. 22, 2011.
Written Opinion of the International Searching Authority from PCT Application No. PCT/US2010/002893, Feb. 22, 2011.
International Search Report from Corresponding PCT Application No. PCT/US2013/066425 dated Mar. 18, 2014.

\* cited by examiner

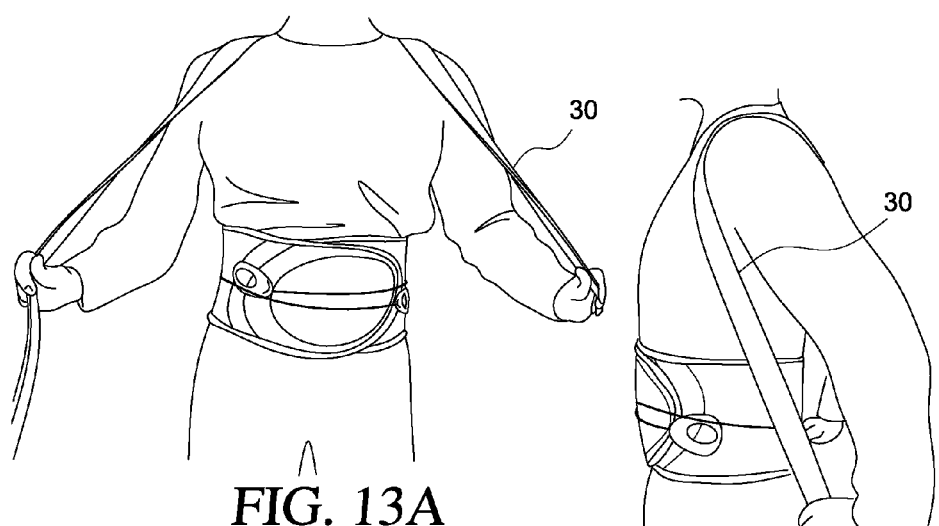
FIG. 13A
FIG. 13B
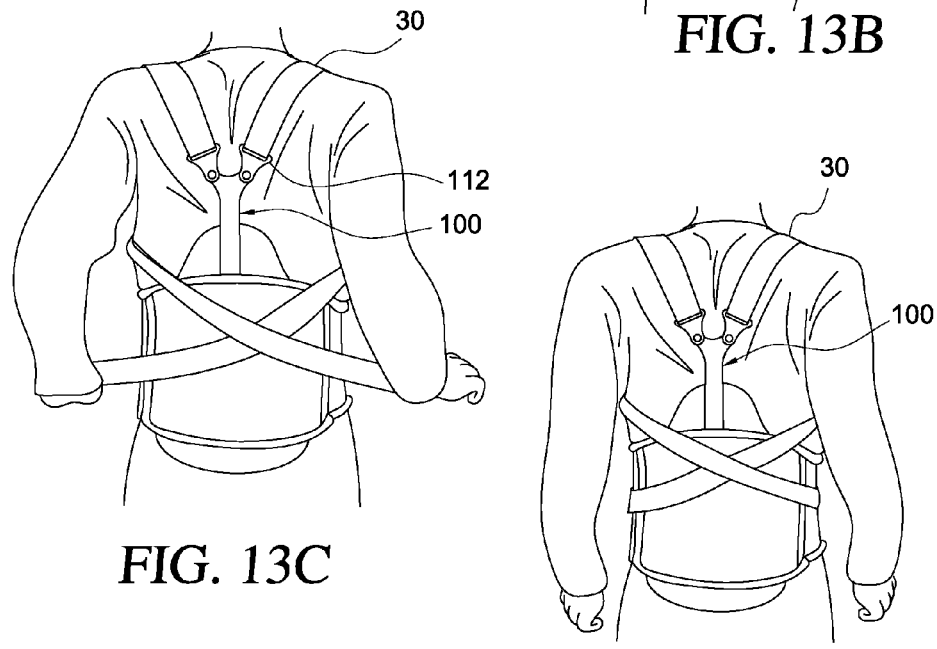
FIG. 13C
FIG. 13D

THORACIC LUMBAR SACRAL ORTHOSIS

CROSS-REFERENCE TO RELATED APPLICATIONS

This application is a continuation of U.S. application Ser. No. 12/938,593, filed on Nov. 3, 2011, which claims the benefit of priority from U.S. provisional application Nos. 61/323,414, filed on Apr. 13, 2010, and 61/258,078, filed on Nov. 4, 2009. Each of these applications are incorporated herein by their entirety.

FIELD OF ART

The application relates generally to an orthopedic device, and more particularly to thoracic lumbar sacral orthosis and methods for installing the same on a wearer.

BACKGROUND

Spinal orthoses are used to treat a variety of conditions associated with the skeletal structure, including such conditions as osteoporosis, back injuries, chest injuries and spinal deformities, by applying pressure to selected positions along the wearer's spine, abdomen and torso. There are different types of spinal orthoses typically categorized by the vertebral level intended for treatment. Spinal orthoses include the sacral orthosis (SO), lumbosacral orthosis (LSO), and the thoraccolumbosacral or thoracic lumbar sacaral orthosis ("TLSO").

The TLSO is designed to provide support and immobilization of the thoracic and lumbar regions following various traumatic injuries or surgical procedures. Indications for use of a TLSO include post-surgical immobilization, herniated disc, spinal stenosis which occurs when the spinal canal narrows and compresses the spinal cord and nerves, spondylolisthesis which occurs due to anterior displacement of a vertebra or the vertebral column in relation to the vertebrae below, spondylolysis or defects of the vertebra, compression fractures, and degenerative spinal pathologies such as osteoporosis.

A variety of different types of TLSO are known in the art. Many TLSO may include flexion control, sagittal control, saggital-coronal control, and triplanar control such that as a person attempts right or left rotation of the thoracic spine, counterforces from the thoracic band and the subclavicular extension limit motion. There are both commercially available TLSO products, and custom-fabricated TLSO types constructed typically from a rigid thermoplastic to form a body jacket.

While either commercially available or custom orthoses devices exist, many of these orthoses are found to be uncomfortable to the wearer and difficult to apply. With commercially available TLSO products, some have the tendency to poorly fit the contours of the wearer, including the spine, which results in an ill-fitting TLSO and ineffectively supports the spine. Many TLSO types, particularly custom-fabricated body jackets, are poorly ventilated and lack sufficient padding. They also lack versatility to enable step-up or step-down treatment of the wearer during the course of treatment. Furthermore, many TLSO products and custom orthoses are not adaptable to provide different forms of control, and are limited to a single type of control.

SUMMARY

In accordance with an embodiment of the invention, a thoracic lumbar sacral orthosis includes an upper body support for use with a torso orthosis, such as a lumbar sacral orthosis, securable about the waist and lumbar region of a wearer. The upper body support has an anterior assembly including an anterior plate secured to the torso orthosis, a sternal assembly connected to the anterior plate, and a pectoral assembly connected to the sternal assembly. A posterior assembly is connected to the torso orthosis and is connected to the pectoral assembly by at least one strap. The sternal assembly has at least one pivot point arranged to pivot the sternal assembly relative to the anterior plate.

According to an embodiment of the sternal assembly, the sternal assembly has at least two pivot points. The pivot points may be defined by lower and upper hinges. A connecting bar is provided between and links the lower and upper hinges to one another. Preferably, each of the hinges is lockable at an angle relative to the connecting bar. From this arrangement of the sternal assembly, the lower hinge is arranged to bias away from the wearer's sternum and the upper hinge is arranged to bias towards the pectoral assembly toward the wearer's chest.

An embodiment of the anterior assembly includes a vertical strut that is slidably secured to the anterior plate at a plurality of predetermined locations, and connects the sternal assembly to the anterior plate. The anterior plate may be connected to the torso orthosis by a strap loop. The anterior plate is movable relative to the torso orthosis by the strap loop.

In an embodiment of the pectoral assembly, the pectoral assembly includes a base part, and first and second arms pivotally mounted to the base part. The first and second arms pivot relative to the base part. The first and second arms may extend obliquely relative to the vertical strut. A ball and joint connection may connect the at least one arm to the pectoral pad so that the pectoral pad is pivotable relative to the pad. At least one rotatable bracket may be attached to the pectoral pad and be arranged to carry the at least one strap.

According to an embodiment of the posterior assembly, the posterior assembly includes a support bar connected to the torso orthosis. The support bar includes rotatable brackets attached thereto, and the at least one strap connects to the posterior assembly via the rotatable brackets to the anterior assembly.

In another embodiment of the posterior assembly, the posterior assembly includes a posterior plate connected to the torso orthosis, and a support panel having an elongate segment adjustably secured to the posterior plate at a plurality of locations. The support panel defines arms extending from the elongate segment such that the arms are securable to the at least one strap connecting to the pectoral assembly. The at least one strap secures to the pectoral assembly, and extends through a slot formed on one of the arms of the support panel, and secures to the torso orthosis. The support panel may be contoured with a spinal portion and a pair of shoulder portions.

The support panel may have a plurality of location points for connection to the posterior plate. The location points may be arranged in a vertical array thereby providing height adjustment of the support panel relative to the posterior plate.

The TLSO in accordance with this disclosure has an anatomical design that follows the contours of the spine, so as to ensure better immobilization and patient comfort. The anterior plate, posterior plate and support panel are provided with ventilation for maximum breathability, and patient compliance by incorporating aerospacer lining and ventilated panels.

Because the upper body support connects to an existing LSO or torso orthosis, the upper body support can be removed after the wearer no longer has need for support by a TLSO. This results in a modular system that enables the upper body support to applied to the torso orthosis when needed, or likewise removed when needed. This results in a step-up and step-down treatment option.

BRIEF DESCRIPTION OF THE DRAWINGS

The inventive orthosis is described with reference to the accompanying drawings which show preferred embodiments according to the orthosis described herein. It will be noted that the orthosis as disclosed in the accompanying drawings is illustrated by way of example only. The various elements and combinations of elements described below and illustrated in the drawings can be arranged and organized differently to result in embodiments which are still within the spirit and scope of the orthosis described herein.

FIGS. 13A-13D are perspective views of a wearer installing the thoracic lumbar sacral orthosis according to the embodiment of FIG. 1 in a second strap configuration.

DETAILED DESCRIPTION OF VARIOUS EMBODIMENTS

A. Overview

Figure 1:
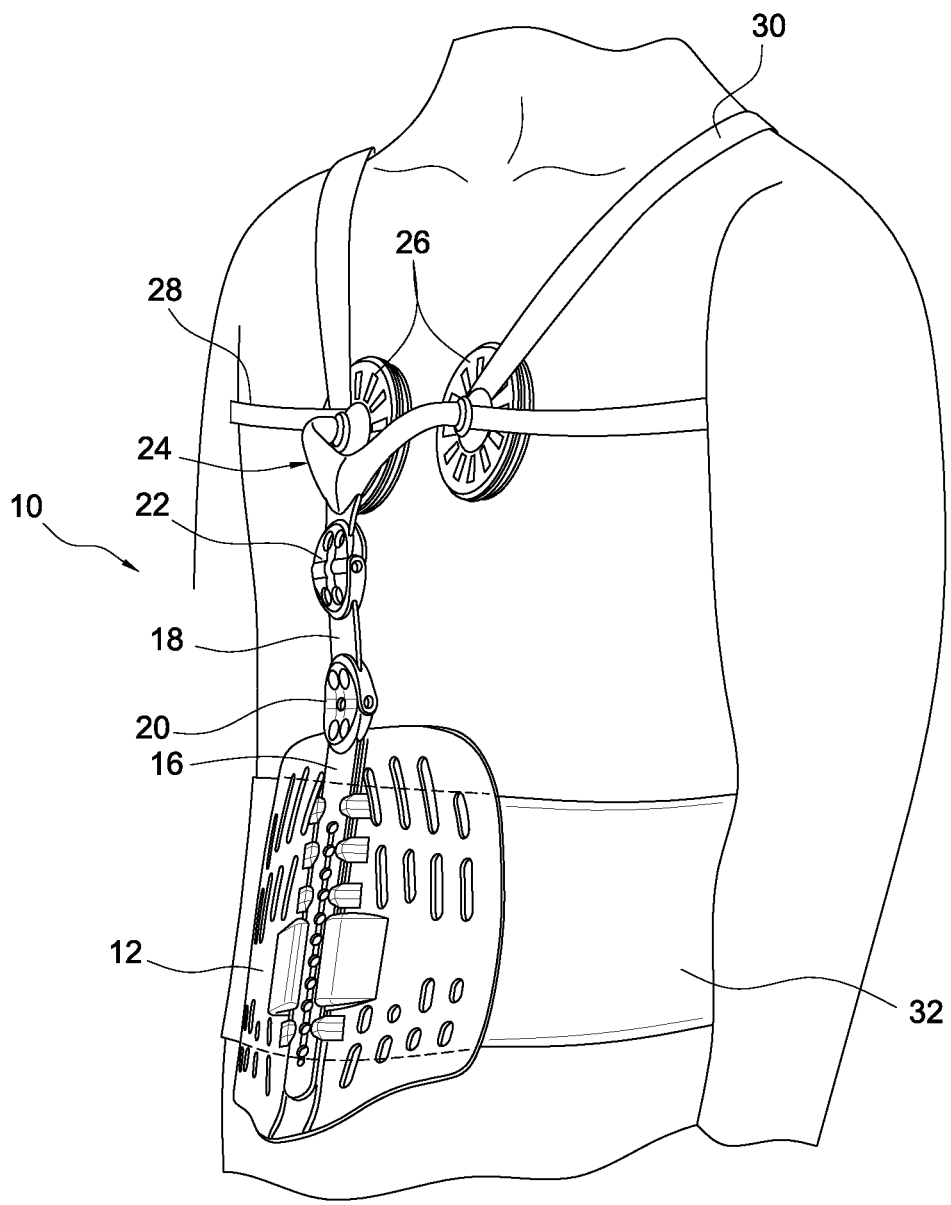
FIG. 1 is a perspective view of a thoracic lumbar sacral orthosis according to an embodiment of the invention.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and are described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. §112, paragraph 6.

The embodiments of the disclosure are particularly adapted for a human body, and may be dimensioned to accommodate different types, shapes and sizes of human body sizes and contours. For explanatory purposes, the orthosis embodiments described herein are referred to as corresponding to different sections of a body and are denoted by general anatomical terms for the human body.

The embodiments of the orthosis are particularly referred to as corresponding to anterior and posterior body sections by an anterior-posterior plane. The anatomical terms described herein are not intended to detract from the normal understanding of such terms as readily understood by one of ordinary skill in the art of orthotics.

B. Various Embodiments of the Orthopedic Device and Components for Use Therewith In observing the embodiment according to FIG. 1, a wearer is shown wearing a thoracic lumbar sacral orthosis (TSLO) 10. The TLSO includes an anterior assembly 11 having an anterior plate 12 connected to a torso orthosis 32, a vertical strut 16 selectively secured to the anterior plate 12, a sternal assembly connected to the vertical strut 16 and having dual pivot points 20, 22, and a pectoral assembly 23 connected to the sternal assembly and having two pectoral pads 26. Straps 28, 30 are used to secure the pectoral assembly to the chest of the wearer and couple to a posterior assembly belonging to the thoracic assembly.

While not described herein in any particularity, the torso orthosis 32 is preferably a lumbar sacral orthosis (LSO) of the type described in U.S. provisional applications 61/155,843 filed on Feb. 26, 2009 and 61/236,649 filed on Aug. 25, 2009, and corresponding U.S. application Ser. No. 12/713,268, filed on Feb. 26, 2010, all of which are incorporated herein in their entirety by reference. Of course, the thoracic assembly may be adapted to fit a variety of different LSO configurations and is not limited to the particular embodiments described in the aforementioned applications.

Figure 2A:
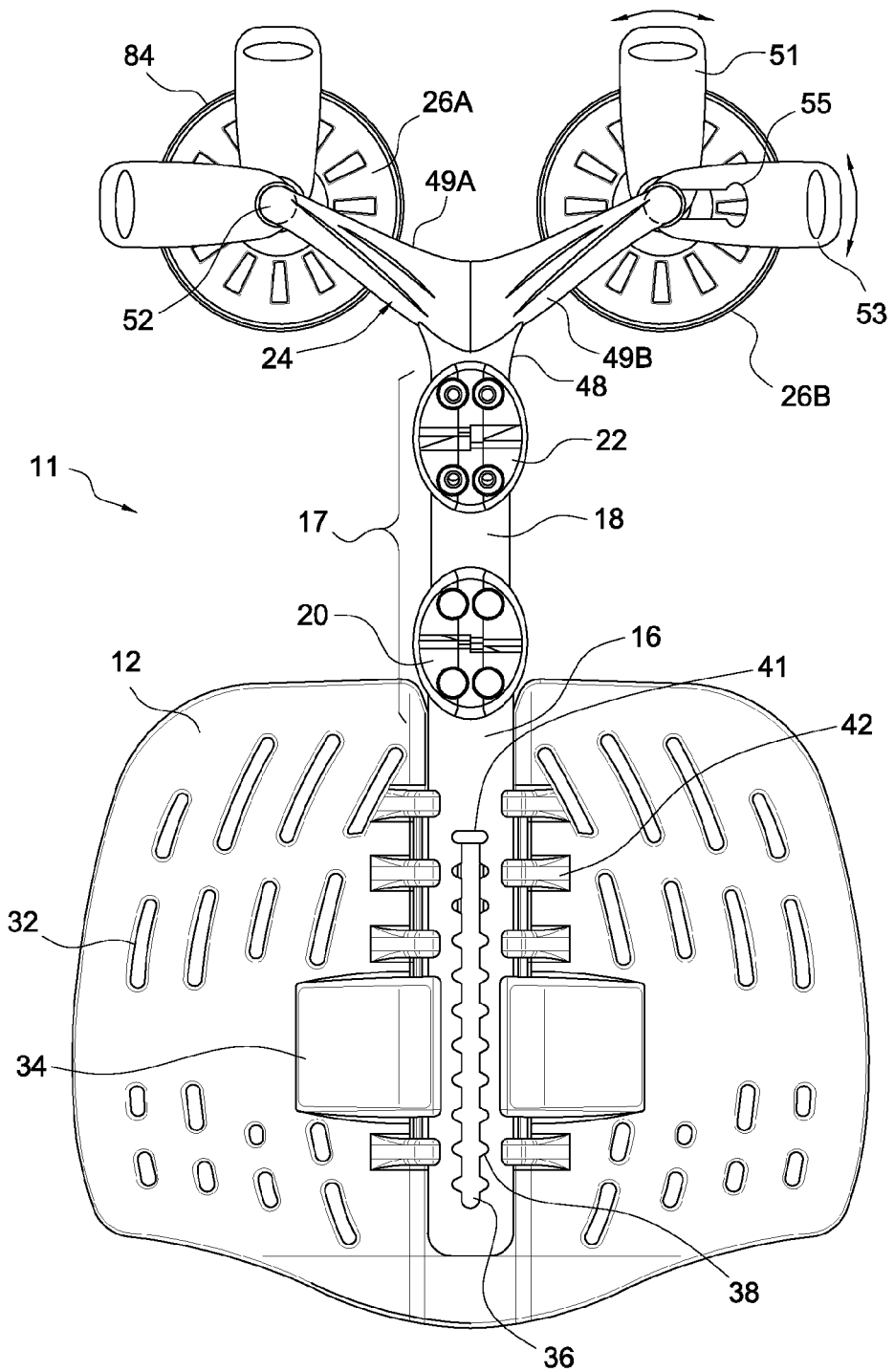
FIG. 2A is a front elevational view of the anterior assembly in FIG. 1.
Figure 2B:
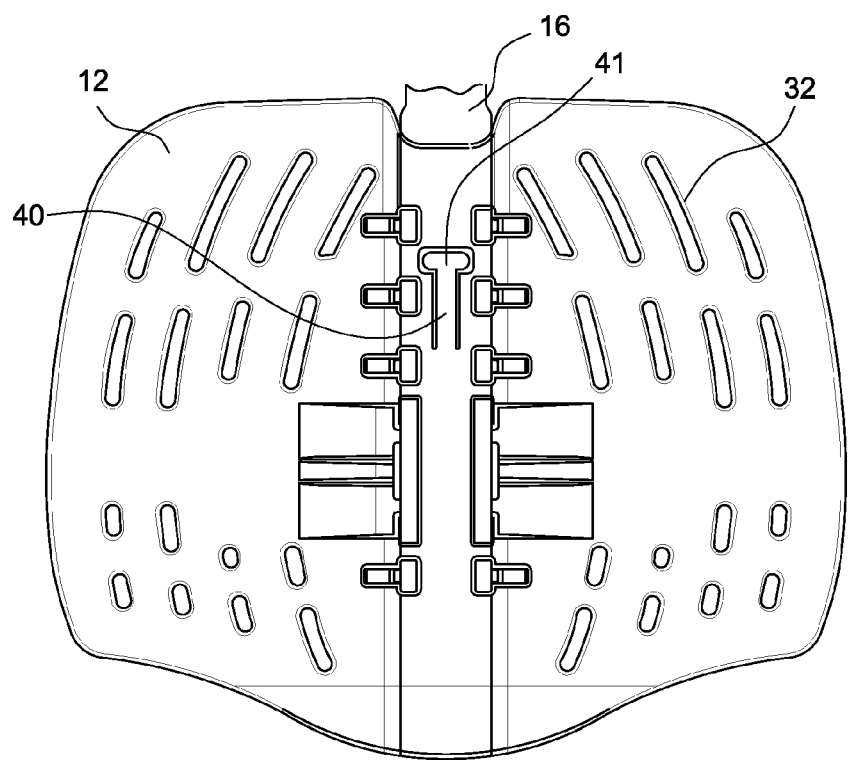
FIG. 2B is a rear sectional elevational view showing the anterior plate of FIG. 2.

As shown in FIGS. 2A and 2B, the anterior plate 12 includes a locking assembly formed along an elongate central portion of the plate 12. The plate 12 defines a plurality of openings 32 which provide for ventilation of the plate against the wearer. The plate 12 is provided with retaining tabs 34, 42 which retain the vertical strut 16 against the plate 12 and which allow the vertical strut 16 to slide relative to the anterior plate 12.

Particularly in observing FIG. 2B, the anterior plate 12 is provided with a tab 40 having a locking head 41 mounted at an end portion thereof. The locking head 41 is biased to extend through locking detents 38 positioned along an elongate slot 36 formed on the vertical strut 16. The vertical strut 16 is arranged to adjust to a plurality of different locations relative to the anterior plate, and the tab allows for simple adjustment yet maintains the vertical strut in a fixed position with respect to the wearer's chest when the wearer's torso flexes.

Figure 3:
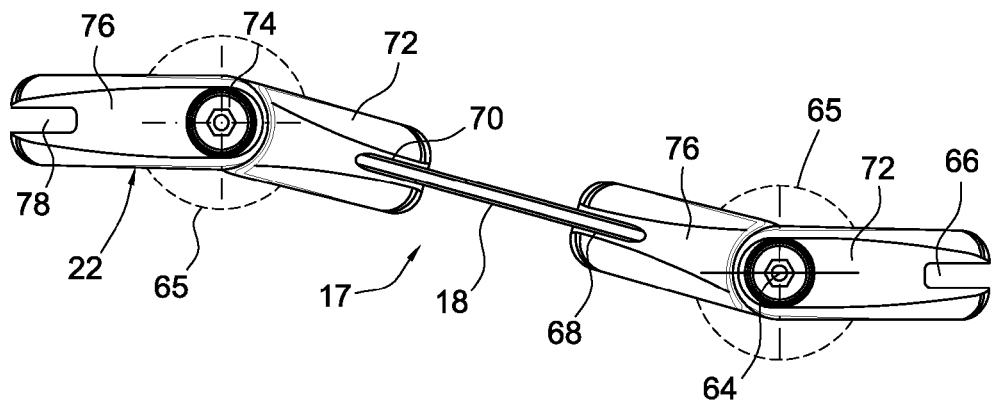
FIG. 3 is a side elevational view of an embodiment of the sternal assembly of FIG. 1.

Turning to the sternal assembly 17, as depicted in both FIGS. 2 and 3, a dual pivot system is provided. Particularly, the pivot points are defined by hinges 20, 22 spaced apart by a connecting bar 18. Each of the hinges 20, 22 is pivotable and lockable to a particular orientation. The connection members may correspond to the connection members described in U.S. patent application Ser. No. 12/264,020 filed on Nov. 3, 2008, and incorporated herein by reference.

Each of the hinges 20, 24 includes a pair of connection members 72, 76 which are arranged to rotate relative to one another about a pivot point 64. Each pair of the connection members is also lockable 74 so as to retain the connection members at an angle 65 relative to one another. In order to provide relative free rotation of the first and second connection members 72, 76 prior to locking the connection members at the angle 65 relative to one another, a biasing member (not shown), such as a spring, is provided between holes formed on corresponding connection members to bias the connecting members away from each other.

The sternal assembly 17 connects to the vertical strut 16 via a slot formed on a lower end of the lower hinge 20, and the pectoral assembly 24 connects to the sternal assembly 17 via a slot 78 formed on an upper end of the upper hinge 22 and a stem 48 extending from the pectoral assembly 24. The lower and upper hinges 20, 22 secure to the connecting bar 18 via a slot 68 formed at an upper end of the lower hinge 20, and via a slot 70 formed at the lower end of the upper hinge 22.

The hinges 20, 22 may be covered with a generally soft overmolded material so as to avoid or minimize any pressure on the wearer's sternum. Likewise, the hinges are fully adjustable so as to modify the angle at which the connecting bar is positioned so as to alleviate pressure on the sternum.

In returning to FIG. 2, the pectoral assembly 24 is shown as including the stem 48 connecting to the sternal assembly 17, a pair of arms 49A, 49B extending obliquely from the stem 48, and a pair of pectoral pads 26A, 26B pivotally mounted to end portions of corresponding arms 49A, 49B. Each of the pectoral pads 26A, 26B includes padding material 84, and a plurality of ventilation openings.

Rotatable strap brackets or D-rings 51, 53 are mounted about each of the pectoral pads 26A, 26B and permit the connection of straps thereto. The brackets 51, 53 may be slidably removable from the pectoral pads 26A, 26B via means such as keyhole openings. Moreover, the brackets 51, 53 may be formed as quick-release buckles which are arranged to secure to corresponding structure carried by straps connecting to a posterior assembly of the thoracic assembly. The brackets may form a key-hole slot 55 to allow for easy removal from the end portions of the arms 49.

Figure 4:
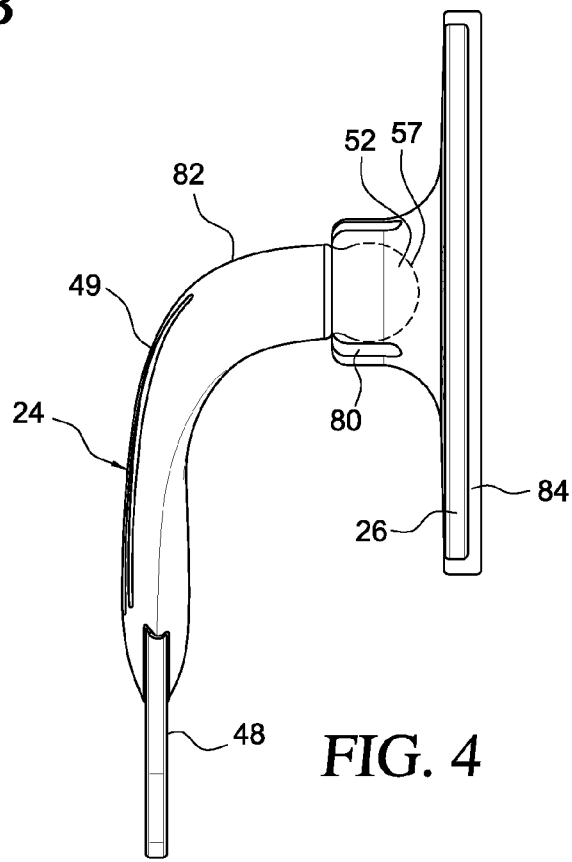
FIG. 4 is a side elevational view of an embodiment of the pectoral assembly in FIG. 1.

Referring to FIG. 4, the pectoral assembly 24 is shown with the arm 49 having a bent portion 82 which biases an end portion defined by a ball 52 into a socket 57 defined by the pectoral pad 26 and secures therewith by a snap fit provided in part by biased openings 80 formed on the pectoral pad. The ball and socket joint permits the pectoral pad to adjust as the wearer moves so as to provide greater comfort and to accommodate movement. Moreover, due to the removability of the pectoral pads, a variety of pectoral pads may be employed which have different sizes or shapes to fit a variety of chest anatomies.

Figure 5:
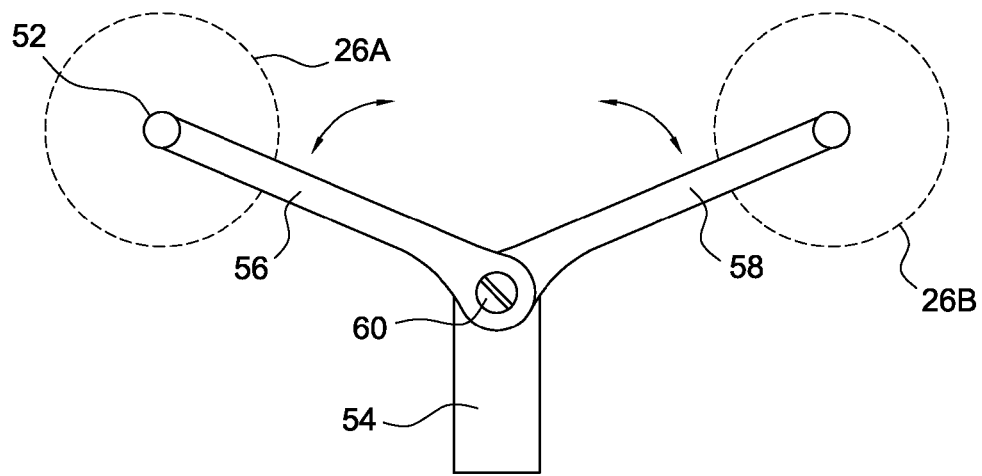
FIG. 5 is a front elevational view of a variation of a pectoral assembly in FIG. 1.

FIG. 5 shows a variation of the pectoral assembly wherein a pair of arms 56, 58 are pivotally connected to a stem 54. The arms 56, 58 may be adjusted relative to one another and the stem 54, so as to accommodate a variety of chest anatomies. A locking device 60 connects the arms 56, 58 to the stem 54 so as to lock an angular configuration of the arms to a particular wearer.

Figure 6:
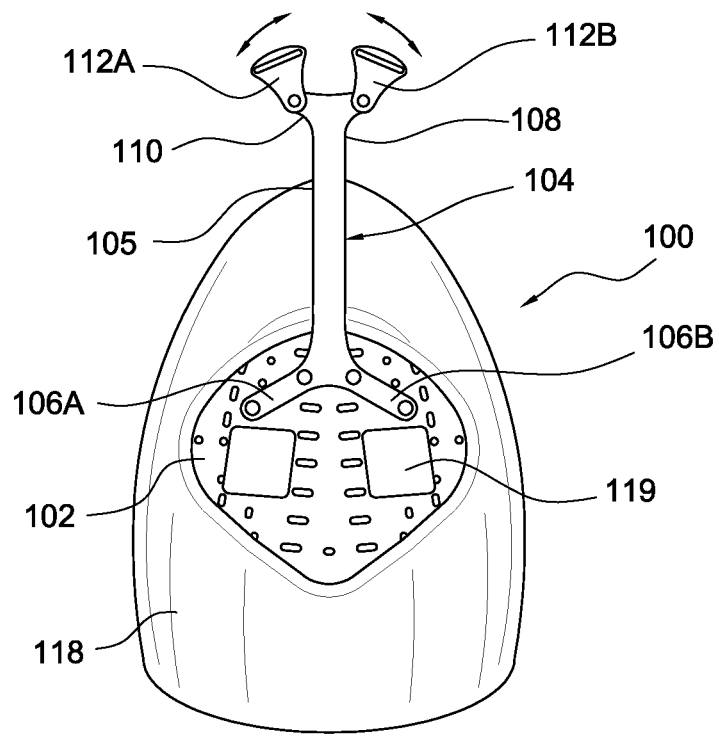
FIG. 6 is a front elevational view of an embodiment of a posterior assembly.

Turning to FIG. 6, an embodiment of a posterior assembly 100 illustrated for use with the embodiments of the anterior assembly described herein. According to this embodiment, the posterior assembly 100 includes a posterior plate 102 having an anatomical contour and is adapted to secure to the torso orthosis. The posterior plate 102 defines a plurality of ventilation openings and a cover 118 that may be placed thereover carrying a cushion element. Mounting pads 119, such as those belonging to a hook and loop system, are also located on the posterior plate for securing to the torso orthosis.

A posterior strut or support bar 104 secures to the posterior plate 102, and defines an elongate center portion 105 and arms 106A, 106B which are mounted onto the posterior plate 102. An upper mount 110 secures to an upper portion 108 of the posterior strut 104, and carries rotatable brackets or D-rings 112A, 112B for securing to straps.

Figure 7:
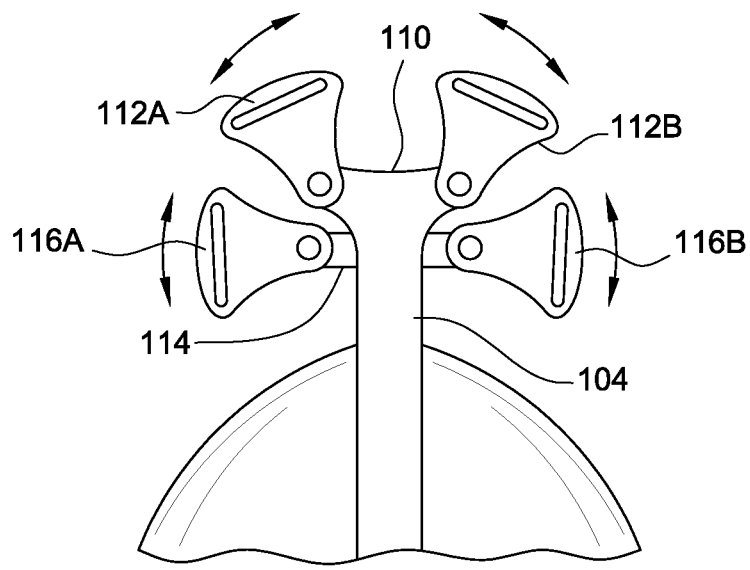
FIG. 7 is a schematic elevational view of a variation of the posterior assembly in FIG. 6.

In a variation shown in FIG. 7, a lateral bar 114 is secured to the upper portion 108 of the posterior strut 104, and carries rotatable brackets or D-rings 116A, 116B for securing to straps.

While the posterior strut 104 is shown as being rigidly secured to the posterior plate, meaning that it is not adjustable, the posterior plate and strut may be configured similarly to the anterior plate and anterior strut shown in FIG. 2 in that the posterior strut is slidably positionable on the posterior plate at a plurality of predetermined locations.

Figure 8A:
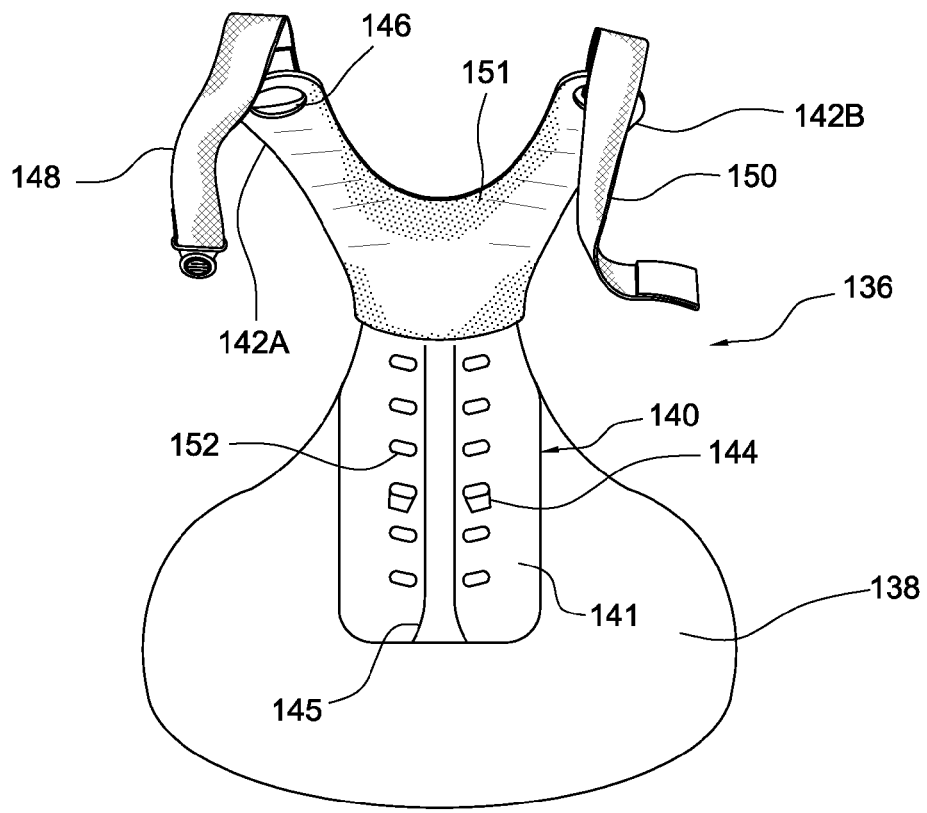
FIG. 8A is a front elevational view of another embodiment of a posterior assembly.

In another embodiment of the posterior assembly, FIG. 8A shows a posterior assembly 136 including a contoured posterior plate or panel 138 similar to the posterior plate 102. In this embodiment, a support panel 140 connects to the posterior plate 138 via a series of incremental slots 152 formed on an elongate segment (141) defined by the support panel 140 and locking tabs 144 formed on the posterior plate 138 or rivets removably securable to the posterior plate. This arrangement allows for adjustment in height of the support panel 140 relative to the posterior plate 138.

The support panel 140 includes a pair of arms 142A, 142B which carry end portions 146 adapted to secure to straps 148, 150.

The support panel may be initially molded flat and then subsequently molded so as to reach over the shoulders, in particular the end portions 146 of the arms. It is noted that the support panel 140 is wider than any of the struts described herein and serves to better distribute pressure over the back and shoulder of the wearer. In addition, the support panel may have an elongate concave contour 145 so as to provide space and contour to the spinal column of the wearer.

Suitable padding 151 may be applied to portions of the support panel, and may likewise be applied to portions of the anterior shell.

Figure 8C:
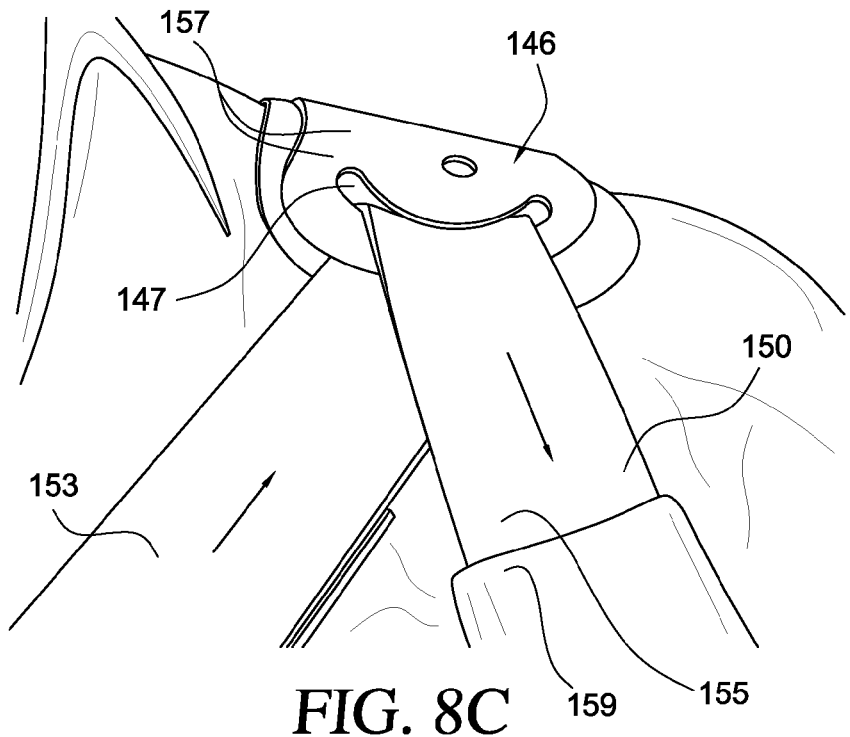
FIG. 8C is a detailed perspective view showing the strapping system according to FIG. 8B.
Figure 8B:
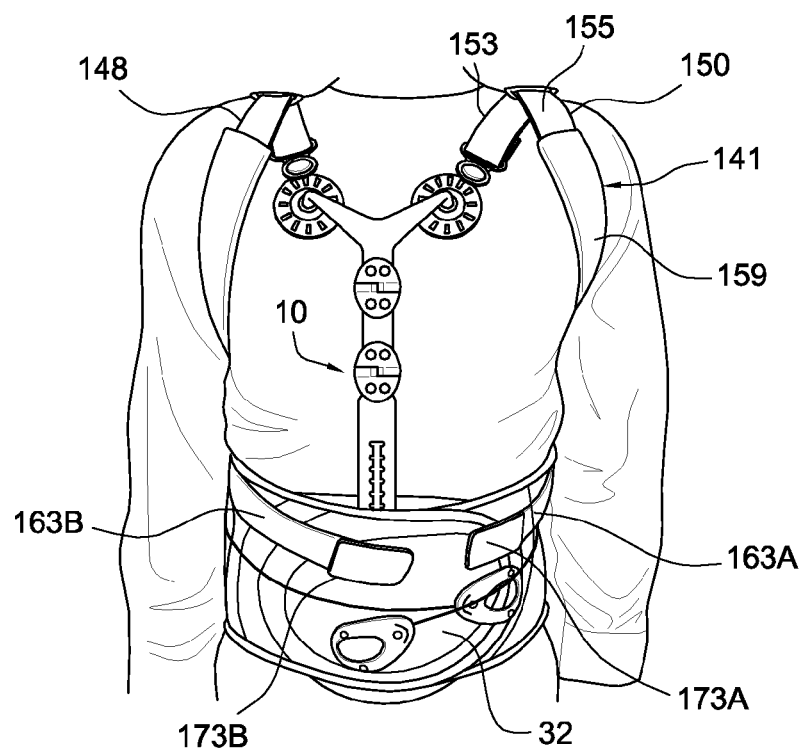
FIG. 8B is a perspective view showing a strapping system on an anterior portion of a wearer for use with the posterior assembly according to FIG. 8A.
Figure 8D:
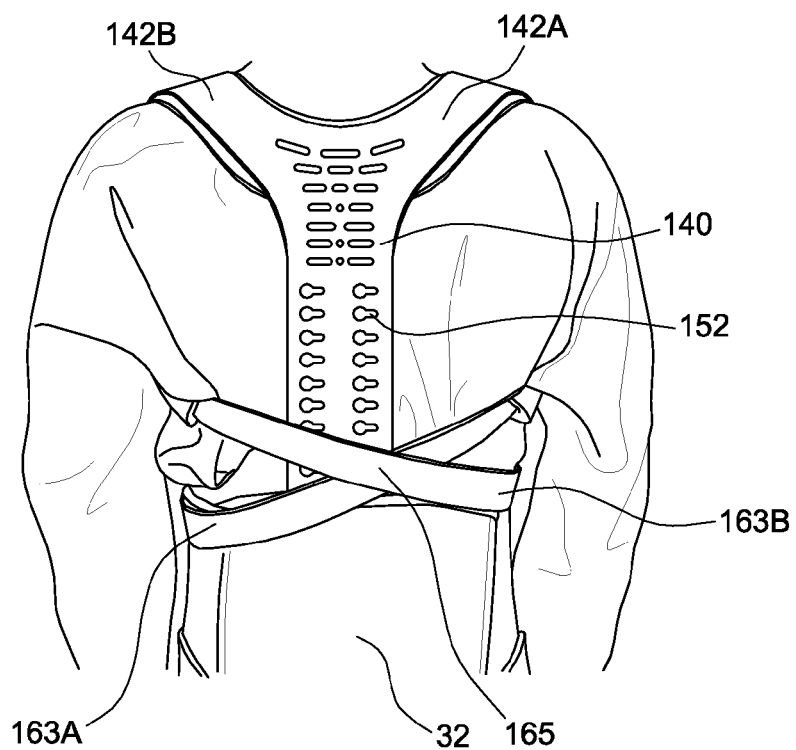
FIG. 8D is a perspective view showing a strapping system on a posterior portion of a wearer for use with the posterior assembly according to FIG. 8A.

Turning to FIGS. 8B-8D, the posterior assembly 136 may be used with a strapping system 141. The end portions 146 of the arms 142A, 142B bend at locations 157 to embrace the shoulder of the wearer, and extend over from the back of the wearer to the frontal portion of the shoulder. The end portions 146 define a slot 147 that is used to receive straps 148, 150 connected to the arms of the thoracic assembly. A padding feature 159 is secured to each of the straps and is intended to underlie the frontal portion of the shoulder, and extend underneath the wearer's armpit.

As particularly shown in FIGS. 8B and 8D, a first segment 153 of the straps 148, 150 begin at the thoracic assembly and extend upwardly to the slots 147 whereat a second segment 150 of the straps is directed downwardly extend underneath the armpit of the wearer. The segments 150 extend downwardly toward the support panel 140 and intersect at intersection point 165 that is located generally within the width of the support panel 140 and at the periphery of the torso orthosis 32. From the intersection point 165, strap segments 163A, 163B are drawn to the frontal aspect of the torso orthosis 32. The strap segments 163A, 163B have end portions 173A, 173B which secure to the torso orthosis 32 via fasteners, such as with hook fasteners if the outer portion of the torso orthosis has loop or hook receiving material.

Figure 8E:
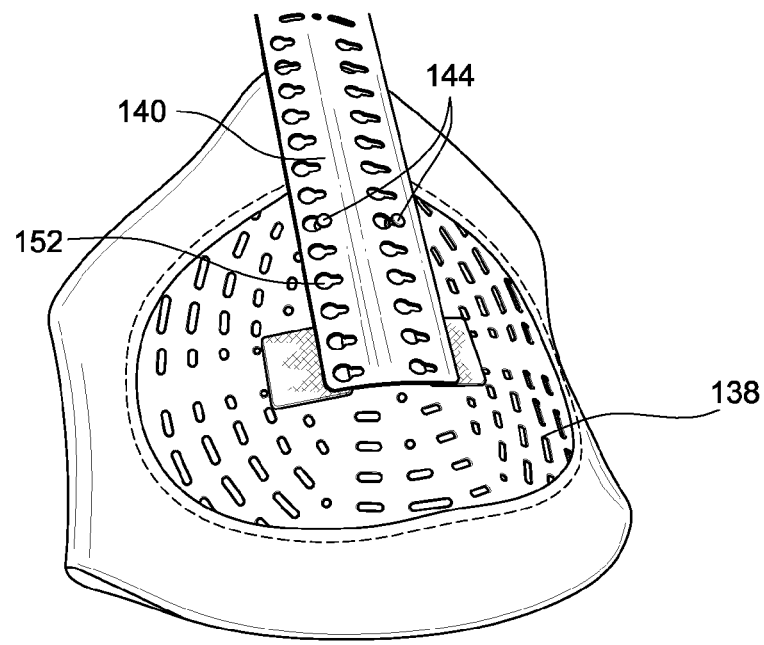
FIG. 8E is a perspective view showing a lower, rear portion of the posterior assembly in FIG. 8A connected to a posterior plate.

FIG. 8E shows the support panel 140 secured to a posterior plate 138 via the slots 152 and locking tabs 144. The posterior plate 138 may include a textile cover to guard it from wearer or to provide greater comfort to the wearer.

Figure 8F:
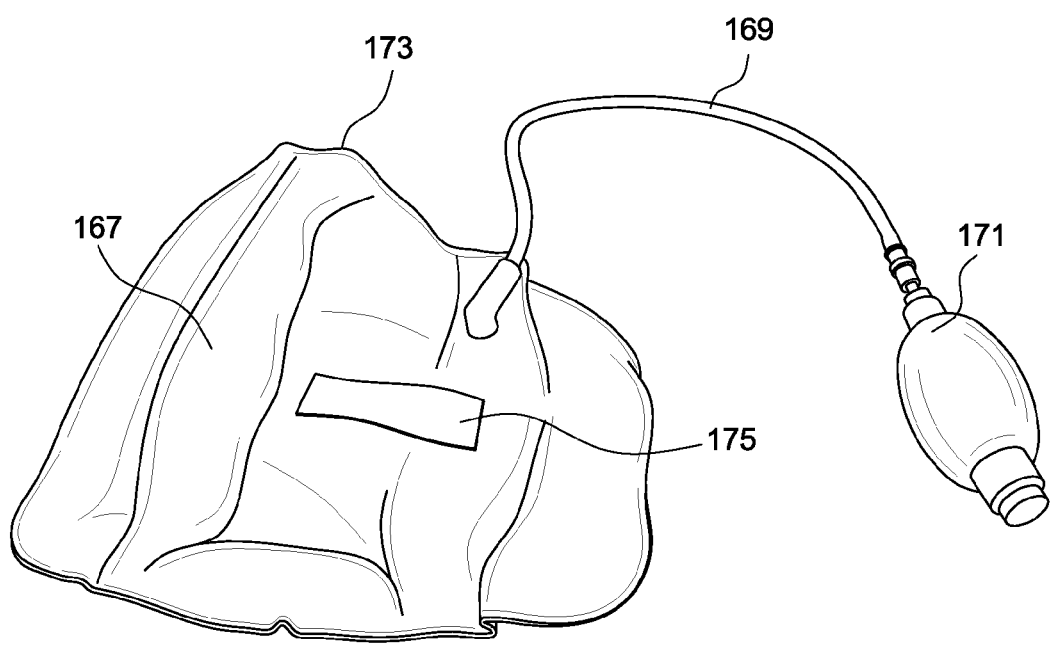
FIG. 8F is a perspective view showing an inflatable pad for use in combination with the posterior assembly and posterior plate according to FIG. 8E.

FIG. 8F depicts an inflatable pad 167 that may be used in combination with the posterior plate 138. The pad 167 is provided with suitable inflation means, such as with a pump 169 allowing the wearer to selectively inflate the pad to a suitable pressure. The pad 167 has a periphery 173 that generally corresponds to the shape of the posterior plate 138. Suitable fastening means, such as a hook and loop system 175, may be used to secure the pad 167 to the posterior plate or the cover of the posterior plate.

In accordance with variations of the TLSO according to the disclosure, only a posterior plate may serve as the posterior assembly, with suitable strapping configurations attached either directly to the posterior plate or to the torso orthosis.

Figure 9:
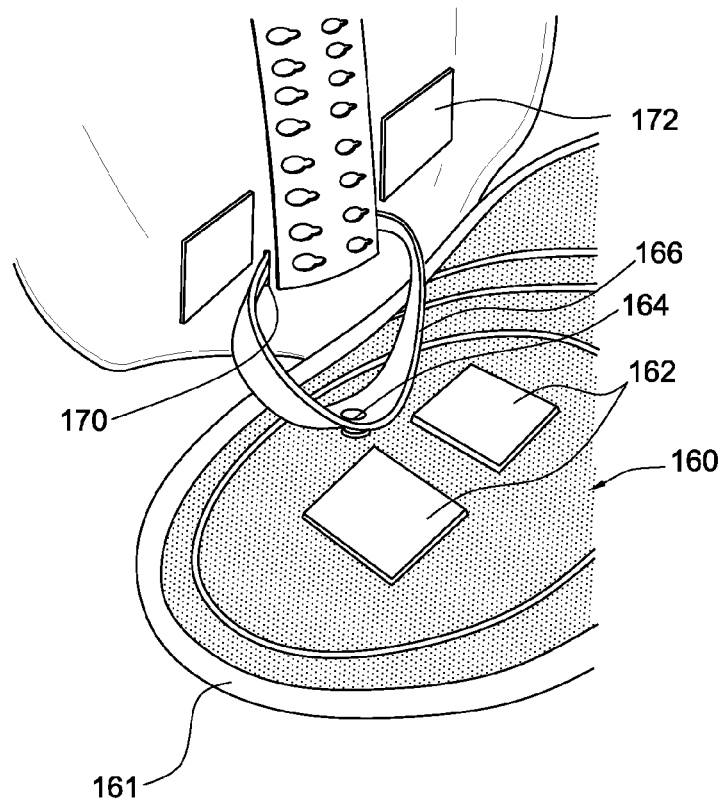
FIG. 9 is a schematic view showing attachment of the outer side of the anterior shell of the thoracic assembly in FIG. 1 to a lumbar sacral orthosis.
Figure 10:
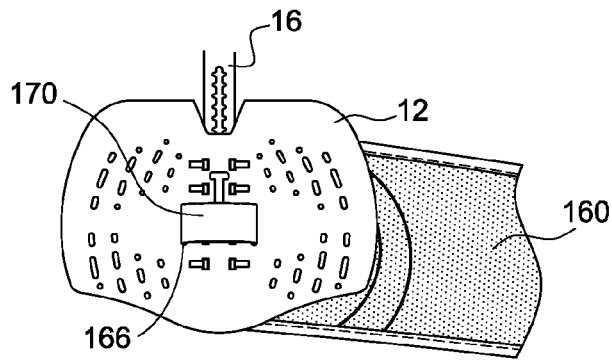
FIG. 10 is a schematic view showing another view of attachment of the thoracic assembly in FIG. 9 to a lumbar sacral orthosis and showing the inner side of the anterior shell.

Referring to FIGS. 9 and 10, the torso orthosis 160 is shown having a belt end portion 161 including attachment pads 162 belonging to a hook and loop system. A strap 166 forming a loop is secured to the belt end portion 161 by a rivet 164. The strap 166 feeds through slots 170 formed on the support panel 12 so as to loosely retain the anterior shell 12 relative to the belt end portion 161. To fully secure the anterior shell 12 to the belt end portion 161, the anterior shell includes attachment pads 172 which engage and removably secure to the attachment pads 162.

Figure 11:
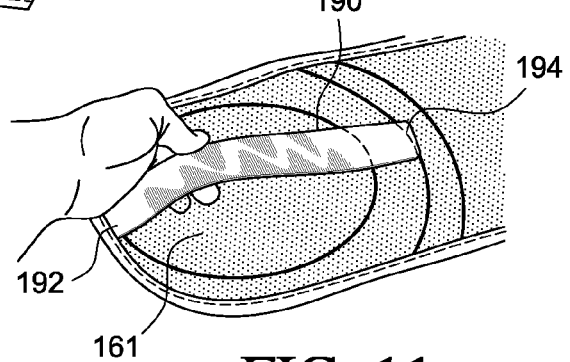
FIG. 11 is a schematic view of a strap mounted on a lumbar sacral orthosis for connecting to the anterior plate or posterior plate of the thoracic assembly in FIG. 1.

According to the variation shown in FIG. 11, a strap 190 may have a first end 192 stitched or fastened to the belt end portion 161 and a second end 194 removably secured to the belt end portion 161. It follows that the second end 194 feeds through the slots formed on the anterior shell and is secured to the belt end portion via fastening means such as hook and loop.

It will be noted that the posterior assembly may be secured to the torso orthosis in any of the aforementioned methods described in connection with the anterior assembly.

In accordance with the embodiments described herein, the TLSO is adjusted to the shape and size of the wearer. An initial step is to adjust the height of the anterior assembly by moving the anterior strut relative to the anterior plate, and locking the anterior strut in position to the anterior plate. A subsequent step is to adjust the pivot points at the lower and upper hinges. The lower hinge is arranged to move away from the chest and the upper hinge is arranged to draw the pectoral plates tightly against the chest of the wearer. Once configured for the patient, any additional adjustments can be conducted according to the aforementioned steps to assure a proper, secure fit.

The pectoral pads are arranged to be rotated away and toward one another depending on the width and height of the chest. Advantageously, the pectoral pads are separated from one another by the arms so as to prevent them from striking the throat of the wearer upon sitting down. Overall, this configuration avoids the common problem in many TLSO products of the orthosis structure riding up on the wearer's body according to the wearer's position.

The TLSO is arranged to allow for a variety of different strapping configurations.

Figure 12A:
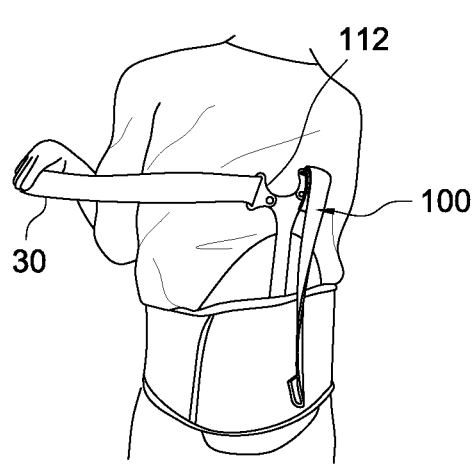
FIGS. 12A-12C are perspective views of a wearer installing the thoracic lumbar sacral orthosis according to the embodiment of FIG. 1 in a first strap configuration.
Figure 12C:
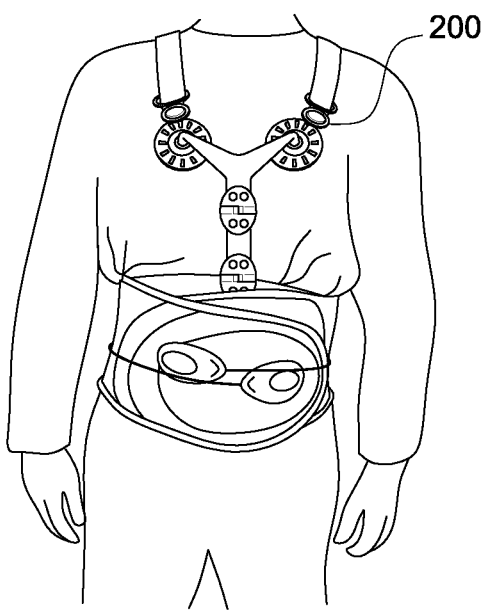
Figure 12B:
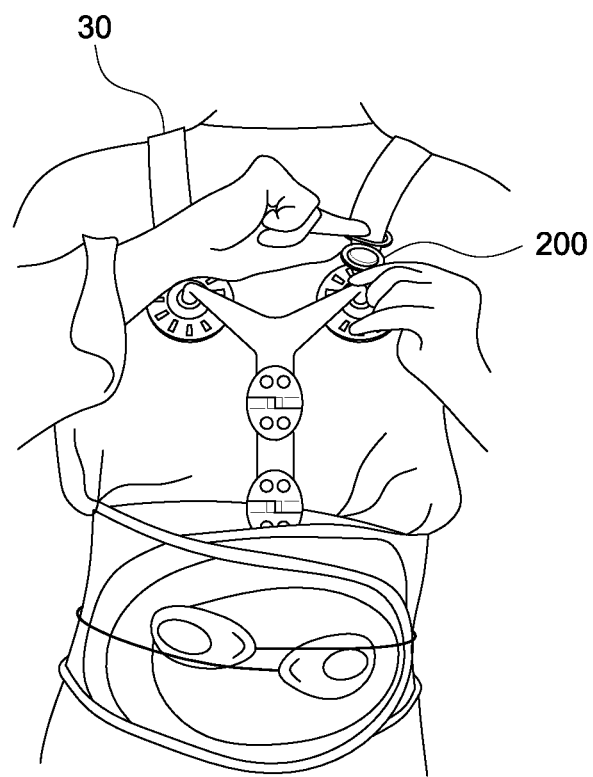
Figure 14A:
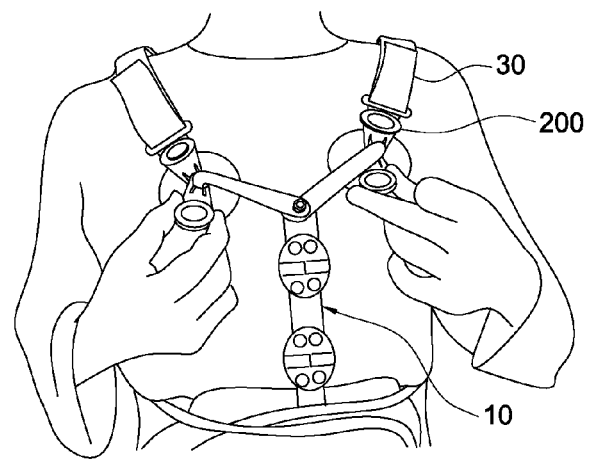
FIGS. 14A-14C are perspective views of a wearer installing the thoracic lumbar sacral orthosis according to the embodiment of FIG. 1 in a third strap configuration.
Figure 14B:
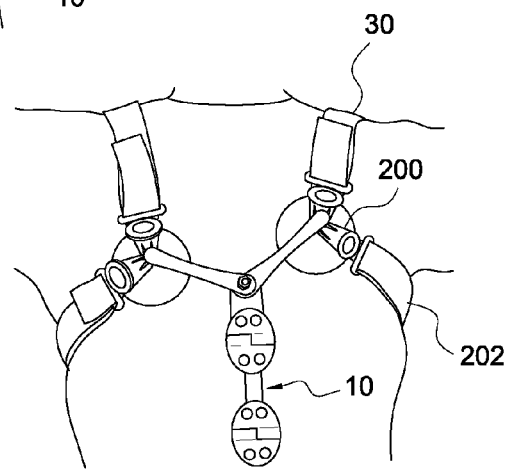
Figure 14C:
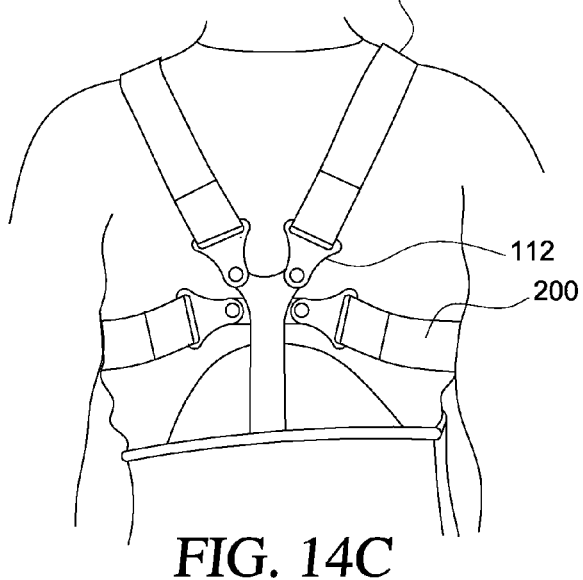

In a first strapping configuration, as exemplified by FIGS. 12A-12C, shoulder straps 30 are secured to brackets 112 on the posterior assembly 100. The straps are pulled over the wearer's shoulder and carry quick release buckles 200. The wearer can adjust the length of the strap which may be done by hook and loop material provided at an end portion of the straps.

A second strapping configuration does not require the anterior assembly. Shoulder straps 30 are secured to brackets 112 on the posterior assembly 100 and these straps are typically longer straps than are used in the first configuration. The straps are crossed over the wearer's shoulder and tightly pulled back toward the wearer's posterior waist. The straps are then crossed in the back of the wearer and subsequently attached to the front of the wearer's anterior waist.

In a third strapping configuration, the shoulder straps 30 connect the posterior assembly to the anterior assembly 10 as in the first strapping configuration. In addition, chest straps 202 are provided and secure to an additional set of brackets mounted on the pectoral assembly, and on the posterior assembly as shown in FIG. 7. The chest straps 202 are subsequently tightened.

These strapping configurations are merely exemplary, and additional configurations may be employed.

The embodiments of the TLSO provide significant advantages for immobilizing a wearer. For example, the anterior thoracic extension achieved in part by the vertical strut 16, when connected to the anterior rigid panel or plate 12, offers saggital plane immobilization against thoraco-lumbar flexion. The posterior thoracic extension realized by the posterior assembly, when connected to the support panel through the locking tabs, and with anterior extension with the shoulder straps, offers additional saggital plane immobilization of both the thoraco-lumbar flexion and extension.

Another advantage, at least from the strapping system according to the embodiments of FIGS. 8A-8D, the straps further enhance triplanar thoraco-lumbar immobilization through (1) maximal sagittal plane immobilization in both flexion and extension, coronal plane immobilization which inhibits thoraco-lumbar lateral bending, and transverse plane immobilization of thoraco-lumbar rotation. The strapping system also offers improved immobilization of the upper thorax through neutral positioning of the shoulders in a retracted position (Shoulders back). This is a key factor in proper posture as well as rotation inhibition of the upper thorax.

While a particular embodiment of an orthopedic device is discussed above, the components of the orthosis described herein may be formed in any suitable manner recognized by a skilled artisan, such as casting, molding, machining, stereolithography, or any other suitable process.

While a particular torso orthosis has been discussed and shown herein, the anterior and posterior assemblies described herein can be adapted to connect and operate with a variety of known torso orthosis known to those skilled in the art. Accordingly, the anterior and posterior assemblies described herein are not limited for use with the exemplary torso orthosis.

As is readily apparent from the foregoing discussion, it is understood that the size of the orthosis and the components thereof can be adjusted so that a large number of different users having different sized joints and body parts may benefit from the present design.

It is also understood that the locations of the various connection points can be alternated from those shown, such that the connection points may be altered from the positions as illustrated herein.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of ordinary skill in this art to construct an orthosis in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. An upper body support for use with a torso orthosis having anterior and posterior sides, the upper body support comprising:
    an anterior assembly having a lower portion connected to the torso orthosis and an upper portion extending upwardly from the lower portion, the anterior assembly including an anterior plate and a sternal assembly mounted on the anterior plate;
    a posterior assembly having a lower portion connected to the torso orthosis, the posterior assembly including a posterior plate connected to the torso orthosis and a support panel removably attached to the posterior plate and extending upwardly from the posterior plate;
    first and second straps connecting to the posterior assembly, the first and second straps each having a first end securable to the sternal assembly, a middle portion passing through strap slots defined by the support panel, and a second end downwardly from the strap slots and removably securing over and onto the torso orthosis.

2. The upper body support of claim 1, wherein the support panel defines an elongate strut and first and second arms extending from the elongate strut, the elongate strut being centrally located between the first and second arms, the first and second arms arranged for extending over a user's shoulder.

3. The upper body support of claim 2, wherein the first and second arms each define an anterior end portion forming a strap slot for receiving a portion of the first and second straps, respectively.

4. The upper body support of claim 3, wherein the sternal assembly includes first and second rotatable buckles, the first and second straps coupling the first and second rotatable buckles.

5. The upper body support of claim 4, wherein each of the first and second rotatable buckles includes a locking part carried by the first and second straps, respectively, and first and second receiving parts rotatably carried by the sternal assembly.

6. The upper body support of claim 2, wherein each of the first and second arms have an anterior end portion defining a curvature arranged to extend at least in part over a user's shoulder.

7. The upper body support of claim 1, wherein the posterior plate defines at least one locking tab arranged to engage at least one slot defined along a strut portion of the support panel.

8. The upper body support of claim 7, wherein the at least one locking tab includes a pair of locking tabs and the at least one slot includes a plurality of pairs of slots along a height of the strut portion.

9. The upper body support of claim 8, wherein the strut portion defines an elongate concave contour generally along its height, the plurality of slots falling outside of the concave contour.

10. The upper body support of claim 7, wherein the plurality of slots are defined as opposed first and second columns of keyhole slots arranged along a height of the strut portion and oriented in a same direction.

11. The upper body support of claim 1, wherein the sternal assembly includes a vertical strut defining an elongate slot including locking detents formed along the length of the elongate slot, the anterior plate including a locking head movable relative to the locking detents, and sized and configured to be locked therewith.

12. The upper body support of claim 11, wherein the anterior plate defines a plurality of retaining tabs arranged in opposed columns and extending over the vertical strut, the vertical strut configured for sliding relative to the retaining tabs while being retained by the retaining tabs to the anterior plate.

13. The upper body support of claim 1, wherein the first ends of the first and seconds straps include fasteners arranged to secure to the anterior side of the torso orthosis.

14. The upper body support of claim 1, wherein the first and second straps are arranged to intersect over the posterior assembly.

15. The upper body support of claim 1, further comprising an inflatable pad securable to and having a profile generally corresponding to a shape of the posterior plate.

16. The upper body support of claim 1, wherein the second ends of the first and second straps secure to a surface at an anterior side of the torso orthosis.

17. An upper body support for use with a torso orthosis having anterior and posterior sides, the upper body support comprising:
    an anterior assembly connected to and extending upwardly relative from the torso orthosis and including an anterior plate and a sternal assembly slidably and lockingly mounted on the anterior plate;
    a posterior assembly connected to the torso orthosis, the posterior assembly including a posterior plate and a support panel removably attached to the posterior plate extending upwardly relative to the torso orthosis;

first and second straps connecting to the posterior assembly, the first and second straps each having a first end securable to the sternal assembly and a middle portion passing through the posterior assembly such that the first and second straps cross over on a posterior side of a user so as to redirect to extend downwardly and secure over and onto the torso orthosis.

18. The upper body support of claim 17, wherein the second ends of the first and second straps secure to a surface at an anterior side of the torso orthosis.

19. An upper body support for use with a torso orthosis having anterior and posterior sides, the upper body support comprising:

an anterior assembly connected to and extending upwardly relative from the torso orthosis and including an anterior plate and a sternal assembly slidably and lockingly mounted on the anterior plate;

a posterior assembly connected to the torso orthosis, the posterior assembly including a posterior plate and a support panel removably attached to the posterior plate and extending upwardly relative to the torso orthosis, the support panel having an elongate strut, and first and second arms extending from the elongate strut, the elongate strut being centrally located between the first and second arms and have a curved profile arranged for extending over a user's shoulder;

first and second straps connecting to the posterior assembly, the first and second straps each having a first end securable to the sternal assembly and a middle portion extending through strap slots defined by the first and second arms and a second end extending downwardly from the strap slots and removably securing over and onto the torso orthosis.

20. The upper body support of claim 19, wherein the second ends of the first and second straps secure to a surface at an anterior side of the torso orthosis.

* * * * *